United States Patent [19]
Keane et al.

[11] Patent Number: 5,841,008
[45] Date of Patent: Nov. 24, 1998

[54] HYDROFLUOROCARBON PRODUCTION USING HEAT CARRIERS IN HIGH TEMPERATURE HYDROGENOLYSIS

[75] Inventors: Thomas R. Keane, Wilmington, Del.; Tiberiu M. Leib, Voorhees, N.J.; William H. Manogue, Newark, Del.; Peter Gideon Gelblum, Philadelphia, Pa.

[73] Assignee: E. I. du Pont de Nemours and Company, Wilmington, Del.

[21] Appl. No.: 836,954

[22] PCT Filed: Nov. 15, 1997

[86] PCT No.: PCT/US95/15105

§ 371 Date: May 22, 1997

§ 102(e) Date: May 22, 1997

[87] PCT Pub. No.: WO96/16009

PCT Pub. Date: May 30, 1996

Related U.S. Application Data

[63] Continuation of Ser. No. 344,434, Nov. 23, 1994, abandoned.

[51] Int. Cl.⁶ .................................................. C07C 19/08
[52] U.S. Cl. ............................................................. 570/176
[58] Field of Search ................................................ 570/176

[56] References Cited

U.S. PATENT DOCUMENTS

| | | | |
|---|---|---|---|
| 3,439,052 | 4/1969 | Bjornson et al | 260/653 |
| 4,451,677 | 5/1984 | Bradley et al | 568/881 |
| 4,754,064 | 6/1988 | Lillwitz | 562/509 |
| 5,208,397 | 5/1993 | Manogue et al | 570/176 |
| 5,254,758 | 10/1993 | Hiles et al | 568/881 |
| 5,300,713 | 4/1994 | Manogue et al | 570/176 |
| 5,364,992 | 11/1994 | Manogue et al | 570/176 |

FOREIGN PATENT DOCUMENTS

| | | |
|---|---|---|
| 670338 | 9/1963 | Canada . |
| 1 578 933 | 5/1977 | United Kingdom . |
| WO 91/05752 | 5/1991 | WIPO . |
| WO 92/18446 | 10/1992 | WIPO . |

OTHER PUBLICATIONS

Satterfield, C.N., "11.1 Commercial Reactors", *Heterogeneous Catalysis in Practice*, 313–315 (1980).

*Primary Examiner*—Alan Siegel

[57] ABSTRACT

This invention relates to a process for the hydrogenolysis of halogenated hydrocarbons containing fluorine together with chlorine and/or bromine.

15 Claims, 1 Drawing Sheet

HYDROFLUOROCARBON PRODUCTION USING HEAT CARRIERS IN HIGH TEMPERATURE HYDROGENOLYSIS

This application is a 371 of PCT/US95/15105 filed Nov. 15, 1995 which is a continuation of 08/344,434 filed Nov. 23, 1994 now abandoned.

BACKGROUND

Halogenated hydrocarbons containing fluorine together with chlorine or bromine have been widely used as refrigerants, propellants, cleaning agents and the like because of their desirable properties such as chemical stability and physiological inactivity. In recent years there have been concerns over the impact of chlorine-containing and bromine-containing materials on the atmosphere and the environment, and wide-ranging restrictions have been put on their production and use. Accordingly, there is currently interest in producing halogenated hydrocarbons of reduced bromine and chlorine content. Hydrogenolysis is a known method for achieving this. For example, U.K. Patent Specification No. 1,578,933 discloses a process for the hydrogenolysis of halogenated ethanes such as $C_2Cl_2F_4$ and $C_2HClF_4$ to produce $C_2H_2F_4$ using conventional hydrogenation catalysts (e.g., palladium supported on alumina or carbon). The reaction is suitably carried out at a temperature not greater than 450° C. (and preferably much lower). PCT Patent Publication No. 91/05752 discloses a process for the hydrogenolysis of various halogenated hydrocarbons containing fluorine (including $C_2Cl_2F_4$ and/or $C_2HClF_4$) at temperatures up to 700° C. The reaction may be carried out in various selected reaction vessels, which may be empty or, in some embodiments, packed with selected materials.

Hydrogenolysis (whether using a conventional hydrogenation catalyst or not) is normally an exothermic reaction. The hydrogenolysis reactor may be operated isothermally or adiabatically. Numerous methods have been used to control the reactor temperature and remove heat from packed-bed catalytic hydrogenolyis reactors. For example, part of the product may be separated and mixed with the reactor feed; an inert gas may be added to the reactor feed; and/or an excess of one reactant may be used. Typically, for hydrogenolyis reactions using packed-bed reactors which are run under adiabatic conditions, high ratios of hydrogen to organic starting material are used and control the reaction temperature (the excess hydrogen acting to absorb the exothermic heat of reaction). In many cases, the use of a large excess of hydrogen as the only control of temperature rise for an adiabatic reaction can reduce the efficiency of the hydrogenolysis reaction as measured by space time yield (i.e., "STY"). Space time yield is defined as the quantity of product formed per unit time per unit reactor volume.

SUMMARY OF THE INVENTION

The present invention provides a process for producing a saturated hydrofluorocarbon (cyclic or acyclic) of the formula $C_nH_aF_b$, wherein n is an integer from 1 to 6, a is an integer from 1 to 7 and b is an integer from 2 to 13, by reacting at least one saturated starting material having the same carbon structure as said saturated hydrofluorocarbon and the formula $C_nH_cX_dF_b$, wherein c is an integer from 0 to 3, d is an integer from 1 to 4, (n and b are as defined above) and each X is independently selected from Cl and Br, with hydrogen in a reaction vessel at a temperature of from about 350° to 700° C. and a pressure of from about 101 kPa to about 7000 kPa for a time sufficient to produce said saturated hydrofluorocarbon. The process is characterized by feeding to the reaction vessel (e.g., a tube) said at least one starting material and, for each mole of total carbon-chlorine and carbon-bromine bonds in said starting material, (a) at least 0.5 moles of hydrogen and (b) at least about 2.5/J moles of a saturated heat carrier compound which has a molar heat capacity greater than the heat capacity of hydrogen and has the formula $C_mH_zF_y$ (where J is the ratio of the molar heat capacity of the heat carrier compound to the molar heat capacity of hydrogen at the reaction temperature) wherein m is an integer from 1 to 4, z is an integer from 0 to 8 and y is an integer from 0 to 10; and reacting said starting material with said hydrogen in said reaction vessel in the presence of said heat carrier compound. In accordance with this invention, the moles of hydrogen plus J times the moles of said heat carrier compound fed to the reaction vessel is at least about 3 times the moles of carbon-chlorine and carbon-bromine bonds in the saturated starting material fed to the reaction vessel, and less than 10% of the fluorine from the carbon-fluorine bonds fed to the reaction vessel is converted to HF.

DETAILED DESCRIPTION

Figure 1:
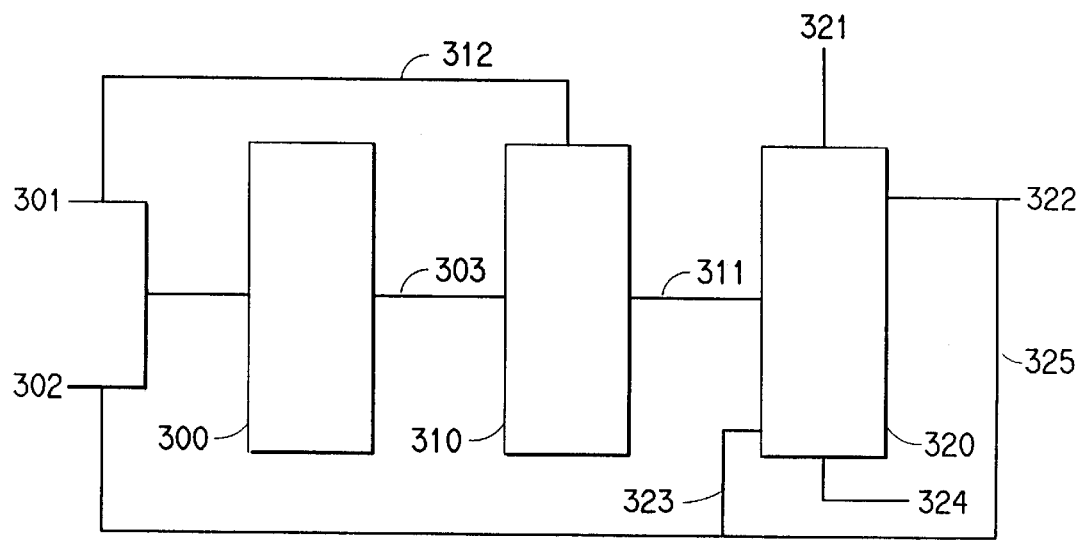
FIG. 1 is a schematic representation of a multiunit process operated in accordance with this invention.

The present invention provides a process for producing a hydrofluorocarbon of the formula $C_nH_aF_b$, wherein n is 1 to 6, a is 1 to 7 and b is 2 to 13. The desired hydrofluorocarbons are saturated and either acyclic (i.e., a+b equals 2n+2) or cyclic (i.e., a+b equals 2n). Examples of such hydrofluorocarbons include compounds where n is 1 (e.g., $CH_2F_2$ and $CHF_3$), compounds where n is 2 (e.g., $CH_3CF_3$, $CHF_2CHF_2$, $CH_2FCF_3$ and $CHF_2CF_3$), compounds where n is 3 (e.g., $CF_3CH_2CF_3$) and compounds where n is 4 (e.g., $CHF_2CF_2CF_2CHF_2$). Of note are embodiments where $CH_2FCF_3$ is produced. The hydrofluorocarbons are produced by contacting saturated halogenated hydrocarbon starting materials having the same number of carbon atoms and fluorine atoms and the same carbon structure (e.g., cyclic or acyclic) as the desired hydrofluorocarbon product, but containing fewer hydrogens than said product (i.e., a fluorohalohydrocarbon of the formula $C_nH_cX_dF_b$, wherein n is 1 to 6, c is 0 to 3, d is 1 to 4, b is 2 to 13, and X is Cl and/or Br) with hydrogen. Of particular note are embodiments where X is chlorine. Examples of suitable starting materials include the following compounds: $CCl_2F_2$, $CHClF_2$, $CClF_3$, $CCl_3CF_3$, $CHCl_2CF_3$, $CH_2ClCF_3$, $CClF_2CClF_2$, $CCl_2FCF_3$, $CHF_2CClF_2$, $CHClFCF_3$, $CF_3CCl_2CF_3$ and $CF_3CHClCF_3$.

The amount of hydrogen fed to the reactor with the starting materials undergoing hydrogenolysis, should be at least 0.5 mole per mole of C—X bond (i.e., carbon-chlorine and carbon-bromine bonds) in said starting materials. Preferably, for high selectivity, the amount of hydrogen ranges from 2 to 20 moles per mole of C—X bond, and more preferably ranges from 5 to 15 moles per mole of C—X bond. The hydrogen can be fed either in the pure state, or diluted with an inert gas of low heat capacity (e.g., nitrogen, helium, or argon) and/or the heat carrier of the present invention. HCl and/or HBr may also be fed, for example, as a result of recycle. If desired, a feed essentially free of HCl and/or HBr can be used.

The heat capacity of hydrogen is about 7 calories per gram mole per degree centigrade at 500° C. (i.e., 7 cal. gmol$^{-1}$ °

$C.^{-1}$ at 500° C.). In accordance with this invention, the reaction of hydrogen with the halogenated hydrocarbon starting material is accomplished in the presence of substantial amounts of a heat carrier compound which has a molar heat capacity at the reaction temperature (i.e., 350° C. to 700° C.) which is a multiple, greater than one, of the hydrogen heat capacity. This multiple is represented herein by J. In accordance with this invention, saturated compounds of the formula $C_mH_zF_y$ (cyclic and acyclic) which have the indicated heat capacity are considered sufficiently stable to function as heat carrier compounds within the reaction temperature range. These include certain hydrocarbons (i.e., compounds where y is 0), fluorocarbons (i.e., compounds where z is 0) and hydrofluorocarbons. Examples of suitable compounds with approximate J values at about 527° C. are: $CH_2F_2$ (2.6), $CHF_3$ (2.9), $CF_4$ (3.1), $CH_3CHF_2$ (4.3), $CH_3CF_3$ (4.6), $CHF_2CHF_2$ (4.8), $CH_2FCF_3$ (4.8), $CHF_2CF_3$ (5.1), $CF_3CH_2CF_3$ (7.1), $CF_3CHFCF_3$ (7.4), $CHF_2CF_2CHF_2$ (7.1), $CH_2FCF_2CF_3$ (7.1), $CHF_2CHFCF_3$ (7.1), $CF_3CF_3$ (5.4), $CF_3CF_2CF_3$ (7.7), cyclo-$C_4F_8$ (8.4), $CH_4$ (2.1), $CH_3CH_3$ (3.7) and $CH_3CH_2CH_3$ (5.3). Of note are embodiments where J multiplied by the number of moles of heat carrier of the formula $C_mH_zF_y$ fed to the reactor is greater than the number of moles of hydrogen fed to the reactor. Also of note are embodiments where the number of moles of heat carrier of the formula $C_mH_zF_y$ fed to the reactor is greater than the number of moles of saturated acyclic starting material of the formula $C_nH_cX_dF_b$ fed to the reactor. Also of note are process embodiments where the heat carrier compound is the same compound as a hydrofluorocarbon being produced.

The following halogenated hydrocarbon hydrogenolysis embodiments represent examples of this invention. $CClF_2CF_3$ (CFC-115) is contacted with hydrogen in a molar ratio of $H_2$:CFC-115 up to about 30:1, preferably about 6:1 to 16:1; and with $CHF_2CF_3$ (HFC-125) in a molar ratio of HFC-125:CFC-115 up to about 10:1, preferably about 1:1 to 2:1. $CCl_3CF_3$ (CFC-113a) is contacted with hydrogen in a molar ratio of $H_2$;CFC-113a up to about 40:1, preferably about 8:1 to 16:1; and with $CH_3CF_3$ (HFC-143a) in a molar ratio of HFC-143a:CFC-113a of up to about 4:1. $CCl_2F_2$ (CFC-12) is contacted with hydrogen in a molar ratio of $H_2$:CFC-12 of up to about 40:1, preferably about 8:1 to 16:1; and with $CH_2F_2$ (HFC-32) in a molar ratio of HFC-32:CFC-12 of up to about 4:1. $CHClFCF_3$ (HCFC-124) is contacted with hydrogen in a molar ratio of $H_2$:CFC-124 of up to about 40:1, preferably about 6:1 to 16:1; and with $CH_2FCF_3$ (HFC-134a) in a molar ratio of HFC-134a:HCFC-124 of up to about 10:1, preferably about 0.5:1 to 4:1. $CCl_2FCF_3$ (CFC-114a) is contacted with $H_2$ in a molar ratio of $H_2$:CFC-114a of up to about 40:1, preferably about 8:1 to 20:1; and with $CF_3CFH_2$ (HFC-134a) in a molar ratio of HFC-134a:CFC-114a of up to about 10:1, preferably about 1:1 to 4:1.

Mixtures of halogenated hydrocarbons may be used.

Suitable mixtures include a mixture of CFC-114a and CFC-114, a mixture of CFC-114a and CFC-133a, a mixture of CFC-114a and HCFC-123, a mixture of CFC-114a and CFC-115, a mixture of CFC-114a and CFC-12, a mixture of CFC-114a and HCFC-22, and a mixture of CFC-114a and CFC-216aa. The following are examples. $CCl_2FCF_3$ (CFC-114a) containing about 2.5 mole percent $CF_2ClCF_2Cl$ (CFC-114) is contacted with $H_2$ in a molar ratio of $H_2$:(CFC-114a plus CFC-114) of up to about 40:1, preferably about 8:1 to 20:1 and with a mixture of $CF_3CFH_2$ (HFC-134a) and $CF_2HCF_2H$ (HFC-134), for example, a 80:20 $CF_3CFH_2$:$CF_2HCF_2H$ mixture, in a molar ratio of (HFC-134a plus HFC-134):(CFC-114a plus CFC-114) of up to about 10:1, preferably about 1:1 to 4:1. $CCl_2FCF_3$ (CFC-114a) containing about 2.5 mole percent $CF_3CCl_3$ (CFC-113a) is contacted with $H_2$ in a molar ratio of $H_2$:(CFC-114a plus CFC-113a) of up to about 40:1, preferably about 8:1 to 24:1 and with $CF_3CFH_2$ (HFC-134a) in a molar ratio of HFC-134a:(CFC-114a plus CFC-113a) of up to about 10:1, preferably about 1:1 to 4:1. $CCl_2FCF_3$ (CFC-114a) containing about 2.5 mole percent $CF_3CCl_2H$ (HCFC-123) is contacted with $H_2$ in a molar ratio of $H_2$:(CFC-114a plus HCFC-123) of up to about 40:1, preferably about 8:1 to 20:1 and with $CF_3CFH_2$ (HFC-134a) in a molar ratio of HFC-134a:(CFC-114a plus HCFC-123) of up to about 10:1, preferably about 1:1 to 4:1. $CCl_2FCF_3$ (CFC-114a) containing about 2.5 mole percent $CClF_2CF_3$ (CFC-115) is contacted with $H_2$ in a molar ratio of $H_2$:(CFC-114 plus CFC-115) of up to about 40:1, preferably about 8:1 to 20:1 and with $CF_3CFH_2$ (HFC-134a) in a molar ratio of HFC-134a:(CFC-114a plus CFC-115) of up to about 10:1, preferably about 1:1 to 4:1. $CCl_2FCF_3$ (CFC-114a) containing about 2.5 mole percent $CF_2Cl_2$ (CFC-12) is contacted with $H_2$ in a molar ratio of $H_2$:(CFC-114a plus CFC-12) of up to about 40:1, preferably about 8:1 to 20:1 and with $CF_3CFH_2$ (HFC-134a) in a molar ratio of HFC-134a:(CFC-114a plus CFC-12) of up to about 10:1, preferably about 1:1 to 4:1. $CCl_2FCF_3$ (114a) containing about 2.5 mole percent $CF_2ClH$ (HCFC-22) is contacted with $H_2$ in a molar ratio of $H_2$:(CFC-114a plus HCFC-22) of up to about 40:1, preferably about 8:1 to 20:1 and with $CF_3CFH_2$ (HFC-134a) in a molar ratio of HFC-134a:(CFC-114a plus HCFC-22) of up to about 10:1, preferably about 1:1 to 4:1. $CCl_2FCF_3$ (114a) containing about 2.5 mole percent $CF_3CCl_2CF_3$ (CFC-216aa) is contacted with $H_2$ in a molar ratio of $H_2$:(CFC-114a plus CFC-216aa) of up to about 40:1, preferably about 8:1 to 20:1 and with $CF_3CFH_2$ (HFC-134a) in a molar ratio of HFC-134a:(CFC-114a plus CFC-216aa) of up to about 10:1, preferably about 1:1 to 4:1.

Other chlorofluorocarbon compounds and hydrochlorofluorocarbon compounds that may be employed in this invention are included in the disclosure of U.S. Pat. No. 5,208,397 and U.S. Pat. No. 5,300,713. Although substantial conversions can be achieved in a once-through system, recycle of unreacted halocarbons or intermediates can be employed (e.g., in the manner disclosed in PCT Patent Publication No. 91/05752).

When d of a starting material of the formula $C_nH_cX_dF_b$ is greater than 1 (i.e., there are multiple C—X bonds in said material), a further aspect of this invention involves feeding to the reaction vessel a second saturated material of the formula $C_nH_eX_fF_b$, where f is an integer less than d (e.g., 1) and e+f equals c+d, and where the fluorine distribution of $C_nH_eX_fF_b$ is the same as the fluorine distribution on the first starting material, $C_nH_cX_dF_b$. For example, if the starting material is $CClF_2CClF_2$, then $CHF_2CClF_2$ may be added to the reactor feed to obtain further improvement in the space-time yields during production of $CHF_2CHF_2$. In one such embodiment for producing $CH_2FCF_3$, the halogenated fluorohydrocarbon, $CCl_2FCF_3$ (CFC-114a) is fed to the reactor with hydrogen in a molar ratio of $H_2$:CFC-114a of from about 4:1 to 22:1, preferably about 16:1 to 20:1; with $CHClFCF_3$ (HCFC-124) in a molar ratio of HCFC-124:CFC-114a of from about 0.4:1 to 1.6:1, preferably about 0.4:1 to 1:1; and with $CH_2FCF_3$ (HFC-134a) in a molar ratio of HFC-134a:CFC-114a of from about 1:1 to 9:1, preferably about 2:1 to 4:1. Preferably, the space time yield for this embodiment is at least about 50 kg/h-m$^3$, more preferably at least about 100 kg/h-m$^3$. In a different embodiment for producing $CHF_2CHF_2$, $CClF_2CClF_2$ (CFC-114) is fed to the reactor with hydrogen in a molar ratio of $H_2$:CFC-114 of from about 4:1 to 22:1, preferably about 16:1 to 20:1; with $CHF_2CClF_2$ (HCFC-124a) in a molar ratio of HCFC-124a:CFC-114 of from about 0.4:1 to 1.6:1, preferably about 0.4:1 to 1:1; and with $CHF_2CHF_2$ (HFC-134) in a molar ratio of HFC-134:CFC-114a of from about 1:1 to 9:1, preferably about 2:1 to 4:1.

Typically, for embodiments where a starting material of the formula $C_nH_cX_dF_b$ (where d is greater than 1) is used together with a second material having the same fluorine distribution of the formula $C_nH_eX_fF_b$, (where f is less than d), the ratio of hydrogen fed to the reaction vessel to C—X bonds in the starting material $C_nH_cX_dF_b$ (e.g., CFC-114a) fed to the reaction vessel is kept within the range of about 2:1 to 11:1, and sufficient $C_nH_eX_fF_b$ compound (e.g., HCFC-124) and heat carrier compound (e.g., HFC-134a) are fed to the reaction vessel to maintain a stable outlet temperature and increase the space time yield by at least about 10% (compared to the space time yield of a reaction at the same stable reaction vessel outlet temperature without feeding heat carrier). Preferably, sufficient $C_nH_eX_fF_b$ and heat carrier are fed to increase the space time yield by at least about 100%. More preferably, sufficient $C_nH_eX_fF_b$ and heat carrier are fed to increase the space time yield by at least about 200%. For example, CFC-114a can be advantageously fed together with HCFC-124 at a mole ratio of CFC-114a:HCFC-124 of about 1:1, HFC-134a at a mole ratio of CFC-114a:HFC-134a of about 1:3, and $H_2$ at a mole ratio of CFC-114a:$H_2$ of about 1:20 to maintain a stable reaction temperature of about 630° C.

The reaction temperature can range from 350° C. to 700° C. Preferably the reaction temperature is at least about 400° C. The temperature of abiabatic operation may be limited by the feed, products and materials of construction. For example, for producing $CH_2FCF_3$ from $CCl_2FCF_3$ and $CHClCF_3$, using $CH_2FCF_3$ heat carrier, in a nickel alloy reactor it is preferred to maintain a temperature no higher than about 630° C. The process pressure is operable over a broad range of pressures. Generally atmospheric (i.e., 101 kPa) or superatmospheric pressures of up to 7000 kPa are employed. Preferably, the pressure is at least about 500 kPa.

The process of the invention provides a means to achieve improved reactor productivity with little degradation of the product hydrofluorocarbon. Preferably, in the process of this invention the yield loss from converting starting materials to hydrocarbons (e.g., $CH_4$ and $C_2H_6$), to carbon and to fluorohydrocarbons containing less fluorine than the halogenated fluorohydrocarbons fed to the reactor is less than about 10%.

The extent of the replacement of halogen by hydrogen increases with reaction time. The reactor residence time is normally between 0.1 seconds and 25 minutes. Preferred residence times are in the range of from about 0.1 minutes to 2 minutes. The reactor residence time will generally be inversely related to the reaction temperature.

Preferably the reaction time and temperature are selected to obtain long term (e.g., greater than about 1000 hours) plug free operation and to provide as the major products of the conversion, products which retain the original ratio of fluorine to carbon. Although substantial conversions can be achieved in a once-through system, recycle of unreacted fluorohalohydrocarbons (or of the intermediate fluorohalohydrocarbons when d is greater than 1) can be employed in a conventional manner. Inert materials and inert products can be recycled as desired.

It is desirable to conduct the conversion of this invention in a reaction vessel which is essentially empty. By "essentially empty" is meant empty or empty except for apparatus such as flow distribution apparatus and/or process control apparatus which does not significantly participate in the conversion process. Accordingly, essentially empty reaction vessels used in this invention are unpacked and are particularly distinguished from reactors which are packed with conventional hydrogenation catalysts, such as palladium on carbon. Low reactor surface to volume ratios are generally preferred.

This invention permits effective operation in a substantially abiabatic manner. By "substantially abiabatic" is meant the heat loss through the reactor walls is a minor proportion (e.g., 10% or less) of the heat generated during the reaction. It is often desirable to conduct the reaction as a substantially adiabatic reaction. Of note are substantially adiabatic reactions where both a starting material of the formula $C_nH_cX_dF_b$, where d is greater than one, (e.g., $CCl_2FCF_3$) and a second material having the same fluorine distribution of the formula $C_nH_eX_fF_b$ where f is less than d are fed to the reaction vessel. Essentially empty reactors may be used for substantially adiabatic reactions.

The conversion of this invention may suitably be conducted in a reaction vessel of at least one metal selected from aluminum, molybdenum, titanium, nickel, cobalt and their alloys. Other suitable reaction vessels include reaction vessels of chromium. Such reaction vessels may also include other materials of construction as long as the surfaces which are in contact with the feed components during the reaction are of the indicated material. The metals may be coated on the inside surface of a reaction vessel (e.g., by plating or sputtering the metals or their alloys onto the inside surface). Such coating can help to minimize corrosion of the reaction vessel wall. A chrome-plated reactor is an example of such a reaction vessel. A liner of such metals on the inside surface of a reaction vessel may also be used. As noted above, an essentially empty reaction vessel is normally employed (i.e., an unpacked vessel which may still contain internals commonly used in empty reactors such as thermocouples and flow distributors such as baffles).

When reference is made to alloys of the metals used in this invention, it is meant a nickel alloy containing from 1 to 99.9% by weight nickel, a cobalt alloy containing 1 to 99.9% by weight cobalt, a molybdenum alloy containing 70 to 99.9% by weight molybdenum, an aluminum alloy containing 80 to 99.9% by weight aluminum, and a titanium alloy containing 72 to 99.8% by weight titanium. Preferably the remainder of these alloys is selected such that the alloy consists essentially of (i) one or more metals selected from aluminum, molybdenum, titanium, nickel, and cobalt, and optionally (ii) iron, copper, chromium and/or tungsten.

Preferred reactor materials for the practice of this invention include nickel and alloys of nickel such as those containing from about 44% to 80% nickel (e.g., Inconel® 600 alloy, Inconel® 617 alloy, Inconel® 625 alloy or Hastelloy® C276 alloy). Suitable nickel alloys include those which contain in addition to nickel, at least one metal selected from Cr, Fe, Co, Mo, W, Nb, Ti, Al, Mn, Cu, V, La, Ti and Zr. They may also contain C, Si and B.

Reference is made to U.S. Pat. No. 5,208,397 and PCT Patent Publication No. 91/05752 for further discussion of reactor materials.

An important feature of the process of the invention is that through selection of the appropriate process conditions, a desired halogenated fluorohydrocarbon hydrogenolysis product can be obtained as the major product with high selectivity and minimal formation of unwanted by-products, especially olefins. Preferably the reaction time, feed material ratios and temperature are selected to obtain long term (i.e., greater than about 1000 hours) plug free operation and to provide as the major product of the conversion, hydrogenolysis product which retains the fluorine content of the starting halogenated hydrocarbon starting material while at least one X is replaced by hydrogen. In many embodiments the reaction time, feed material ratios and temperature are controlled so that at least about 90% of conversion product has the same number of fluorine atoms as the halogenated hydrocarbon starting material.

Preferably, in the process of this invention, the yield loss from conversion of halogenated hydrocarbons to non-halogenated hydrocarbons (e.g., $CH_4$, $C_2H_6$ or carbon) is less than 10%. The process can be operated such that the formation of solids in the reaction vessel is low, thus permitting long-term operation with infrequent plugging.

The products of the reaction can be separated and purified by conventional means (e.g., distillation or sorption). The products can be used as refrigerants, heat transfer media, foam expansion agents, aerosol propellants, solvents and power cycle working fluids.

FIG. 1 illustrates employment of the instant invention to produce $CH_2FCF_3$ (HFC-134a). In the illustrated method, $CCl_2FCF_3$ (CFC-114a) from feedline (302) is fed along with hydrogen from feedline (301) to a reactor (300) constructed and operated in accordance with this invention. The converted products are fed through line (303) to a separation system such as distillation column or partial condenser (310) with hydrogen, uncondensed organics and a portion of the HCl being removed through line (312) and recycled back to the hydrogenolysis reactor (300). The rest of the products consisting essentially of HCl, CFC-114a, HCFC-124 ($CHClFCF_3$) and HFC-134a is fed through line (311) to another separation zone (320) where HCl is removed through line (321), a portion of the HFC-134a and HCFC-124 is removed through line (322) for further purification, the remainder of the HFC-134a and HCFC-124 is recycled back to reactor (300) through line (325), CFC-114a is removed through line (323) and recycled back to the reactor (300), and high boilers are removed through line (324). Alternatively, HCFC-124 and HFC-134a can be separately removed from the separation zone (320), with a portion of each being separately recycled through line (325); and/or CFC-114a together with a portion of the HCFC-124 can be recycled through line (323).

Figure 2:
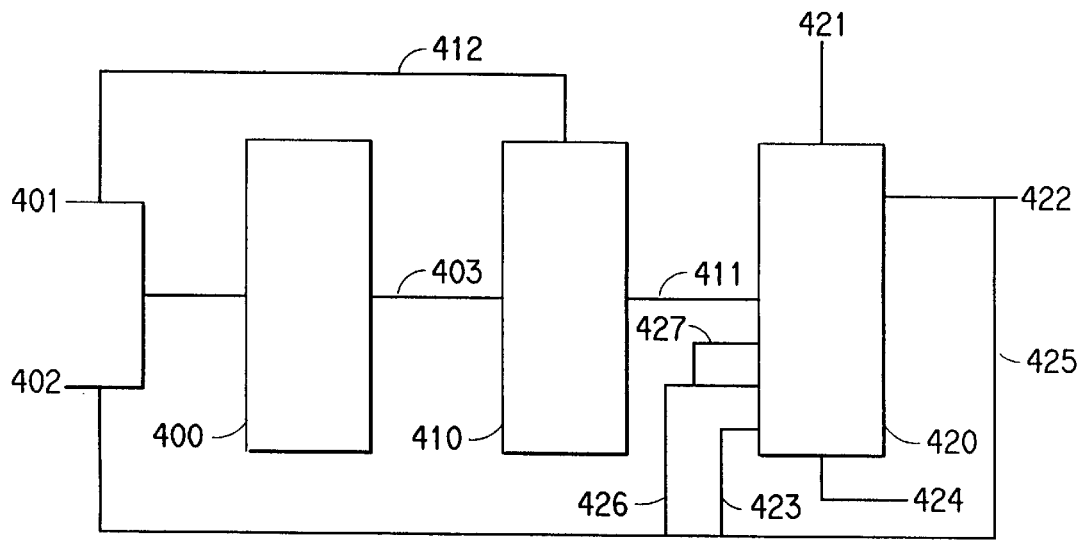
FIG. 2 is a schematic representation of a multiunit process operated in accordance with this invention.

FIG. 2 illustrates employment of the instant invention to produce $CH_3CF_3$ (HFC-143a). In the illustrated method, $CCl_3CF_3$ (CFC-113a) from feedline (402) is fed along with hydrogen from feedline (401) to a reactor (400) constructed and operated in accordance with this invention. The converted products are fed through line (403) to a separation system such as distillation column or partial condenser (410) with hydrogen, uncondensed organics, and a portion of the HCl being removed through line (412) and recycled back to the hydrogenolysis reactor (400). The rest of the products consisting essentially of HCl, CFC-113a, $CHCl_2CF_3$, (HCFC-123), $CH_2ClCF_3$ (HCFC-133a) and HFC-143a is fed through line (411) to another separation zone (420) where HCl is removed through line (421), a portion of the HFC-143a is removed through line (422) for further purification, the remainder of the HFC-143a is recycled back to reactor (400) through line (425), HCFC-133a is removed through line (427) and recycled back to reactor (400), HCFC-123 is removed through line (426) and recycled back to reactor (400), CFC-113a is removed through line (423) and recycled back to the reactor (400), and high boilers are removed through line (424). Alternatively, HCFC-123 may be at least partially recovered from the separation zone (420) as a co-product.

Those skilled in the art will recognize that since the drawings are representational, it will be necessary to include further items of equipment in an actual commercial plant, such as pressure and temperature sensors, pressure relief and control valves, compressors, pumps, storage tanks and the like. The provision of such ancillary items of equipment would be in accordance with conventional chemical engineering practice.

Practice of the invention will become further apparent from the following non-limiting examples.

EXAMPLES

A flow reactor under computer control was used. The reactor was an empty 6" (15.2 cm) i.d.×8' (244 cm) long nickel alloy tube only containing baffles to insure uniform flow. Electric heaters were used to provide a substantially adiabatic operation.

Results of various experiments are shown in Table 1. Run No. 1 was not done using the the reaction conditions of this invention and is a comparison experiment.

TABLE 1

| Run. No. -> | 1 | 2 | 3 | 4 | 5 | 6 | 7 |
|---|---|---|---|---|---|---|---|
| Temp. °C., | | | | | | | |
| Inlet | 486 | 517 | 533 | 550 | 517 | 504 | 513 |
| Outlet | 617 | 615 | 619 | 619 | 618 | 616 | 619 |
| Pressure psig | 307 | 325 | 334 | 374 | 318 | 418 | 418 |
| (kPa) | (2220) | (2340) | (2400) | (2680) | (2290) | (2980) | (2980) |
| CFC-114a Feed Rate, lb/h | 4.0 | 17.9 | 16.3 | 13.0 | 13.5 | 16.0 | 16.4 |
| (kg/h) | (1.8) | (8.1) | (7.4) | (5.9) | (6.1) | (7.3) | (7.4) |
| [$H_2$]:[CFC-114a] | 25.9 | 4.27 | 10.7 | 11.1 | 20.6 | 17.1 | 10.6 |
| [$H_2$]:[HCl] | 2.88 | 2.75 | 4.07 | 6.21 | 2.31 | 4.47 | 5.11 |
| [HCFC-124]:[CFC-114a] | 0.38 | 1.42 | 1.03 | 1.00 | 1.06 | 1.19 | 1.03 |
| [HFC-134a]:[CFC-114a] | 0.41 | 3.42 | 4.66 | 8.30 | 3.11 | 2.14 | 4.08 |
| CFC-114a % conv. | 99.9 | 84.4 | 94.4 | 97.1 | 96.4 | 96.8 | 96.4 |
| HCFC-124 sel. (mole %) | NA | 31.5 | 17.3 | 8.0 | 7.5 | NA | 7.0 |
| HFC-134a sel. (mole %) | 99.6 | 68.4 | 82.5 | 90.9 | 92.2 | 99.3 | 92.7 |
| HFC-134a STY, lb/h-ft$^3$ | 1.9 | 6.4 | 6.4 | 6.0 | 6.0 | 8.1 | 8.0 |
| (kg/h-m$^3$) | (30.4) | (103) | (103) | (96.1) | (96.1) | (130) | (128) |

What is claimed is:

1. A process for producing a saturated cyclic or acyclic hydrofluorocarbon of the formula $C_nH_aF_b$, wherein n is an integer from 1 to 6, a is an integer from 1 to 7 and b is an integer from 2 to 13, by reacting at least one saturated starting material having the same carbon structure as said saturated hydrofluorocarbon and the formula $C_nH_cX_dF_b$, wherein c is an integer from 0 to 3, d is an integer from 1 to 4, and each X is independently selected from Cl and Br, with hydrogen in a reaction vessel at a temperature of from about 350° to 700° C. and a pressure of from about 101 kPa to about 7000 kPa for a time sufficient to produce said saturated hydrofluorocarbon, characterized by:

feeding to the reaction vessel, said at least one starting material and, for each mole of total carbon-chlorine and carbon-bromine bonds in said starting material, both (a) at least 0.5 moles of hydrogen, and (b) at least about 2.5/J moles of a heat carrier compound which has a molar heat capacity greater than the molar heat capacity of hydrogen and the formula $C_mH_zF_y$, where J is the ratio of the molar heat capacity of the heat carrier compound to the molar heat capacity of hydrogen at the reaction temperature, wherein m is an integer from 1 to 4, z is an integer from 0 to 8 and y is an integer from 0 to 10; and reacting said starting material with said hydrogen in said reaction vessel in the presence of said heat carrier compound; the moles of hydrogen plus J times the moles of said heat carrier compound fed to the reaction vessel being at least about 3 times the moles of carbon-chlorine and carbon-bromine bonds in the saturated starting material fed to the reaction vessel, and less than 10% of the fluorine from the carbon-fluorine bonds fed to the reaction vessel being converted to HF.

2. The process of claim 1 wherein the reaction vessel is essentially empty.

3. The process of claim 2 wherein the reaction is conducted as a substantially adiabatic reaction.

4. The process of claim 2 wherein X is chlorine.

5. The process of claim 2 wherein the reactor is nickel or an alloy containing from 44 to 80% nickel.

6. The process of claim 2 wherein $CH_2FCF_3$ is produced.

7. The process of claim 1, claim 2, or claim 3 wherein the starting material includes a starting material where d is greater than one and a second material of the formula $C_nH_eX_fF_b$ where f is an integer less than d, where e+f is equal to c+d, and where the fluorine distribution on said second material is the same as the fluorine distribution on the first starting material.

8. The process of claim 7 wherein $CH_2FCF_3$ is produced and wherein $CCl_2FCF_3$ is fed to the reactor with hydrogen in a molar ratio of $H_2:CCl_2FCF_3$ of from about 4:1 to 22:1, with $CHClFCF_3$ in a molar ratio of $CHClFCF_3:CCl_2FCF_3$ of from 0.4:1 to 1.6:1 and with $CH_2FCF_3$ in a molar ratio of $CH_2FCF_3:CCl_2FCF_3$ of from about 1:1 to 9:1.

9. The process of claim 8 wherein sufficient $C_nH_eX_fF_b$ compound and heat carrier compound is fed to the reaction vessel to maintain a stable outlet temperature and increase the space time yield by at least about 100%.

10. The process of claim 8 wherein the space time yield is at least about 50 kg/h-m³.

11. The process of claim 7 wherein sufficient $C_nH_eX_fF_b$ compound and $C_mH_zF_y$ heat carrier are fed to the reaction vessel to maintain a stable outlet temperature and increase the space time yield by at least 10% compared to the space time yield of a reaction at the same stable outlet temperature without feeding heat carrier.

12. The process of claim 11 wherein sufficient $C_nH_eX_fF_b$ compound and CmHzFy heat carrier are fed to increase the space time yield by at least about 100%.

13. The process of claim 11 wherein the first starting material is $CF_3CCl_2F$ and the second material is $CF_3CHClF$.

14. The process of claim 13 wherein the heat carrier is $CF_3CH_2F$.

15. The process of claim 13 wherein the heat carrier is $CH_4$.

* * * * *